United States Patent [19]

Koch et al.

[11] Patent Number: 5,021,578
[45] Date of Patent: Jun. 4, 1991

[54] CERTAIN PERFLUOROLOWERALKOXY-2-PYRIDYLOXY PROPIONATES HAVING HERBICIDAL ACTIVITY

[75] Inventors: Volker Koch, Kelkheim; Lothar Willms, Hillscheid; Andreas Fuss, Karlstein; Klaus Bauer, Rodgau; Hermann Bieringer, Eppstein/Taunus; Helmut Bürstell, Frankfurt am Main, all of Fed. Rep. of Germany

[73] Assignee: Hoechst Aktiengesellschaft, Frankfurt am Main, Fed. Rep. of Germany

[21] Appl. No.: 314,319

[22] Filed: Feb. 22, 1989

Related U.S. Application Data

[63] Continuation of Ser. No. 944,324, Dec. 19, 1986, abandoned.

[30] Foreign Application Priority Data

Dec. 21, 1985 [DE] Fed. Rep. of Germany ....... 3545571

[51] Int. Cl.$^5$ .................. C07D 213/69; C07D 413/12; A01N 43/40
[52] U.S. Cl. .................... 546/296; 546/275; 546/283; 546/291; 544/96; 71/94
[58] Field of Search ............................ 546/296; 71/94

[56] References Cited

U.S. PATENT DOCUMENTS 3,810,752 5/1974 Wilcox ................................. 71/94
4,300,944 11/1981 Bohner et al. ...................... 71/94
4,503,061 3/1985 Bristol ................................ 514/338
4,606,757 8/1986 Malhotra et al. .................... 71/94

OTHER PUBLICATIONS

"The Chemistry of Heterocyclic Compounds", cover pages, introduction, Chapter IV.

Primary Examiner—Alan L. Rotman
Attorney, Agent, or Firm—Curtis, Morris & Safford

[57] ABSTRACT

Compounds of the formula

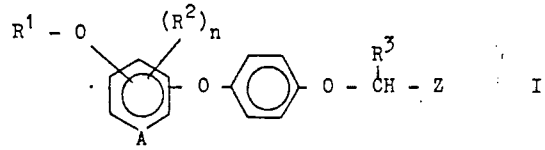

in which $R^1$ denotes haloalkyl, haloalkenyl or haloalkynyl, $(R^2)_n$ denotes H or up to 3 halogens, A denotes N or N→O, $R^3$ denotes H or alkyl, and Z denotes, inter alia, a carboxyl group or a functional derivative thereof, are valuable herbicides and growth regulators.

9 Claims, No Drawings

CERTAIN PERFLUOROLOWERALKOXY-2-PYRIDYLOXY PROPIONATES HAVING HERBICIDAL ACTIVITY

This application is a continuation of application Ser. No. 944,324, filed Dec. 19, 1986, now abandoned.

The present invention relates to novel heterocyclic substituted 4-phenoxyalkanecarboxylic acid derivatives of the general formula

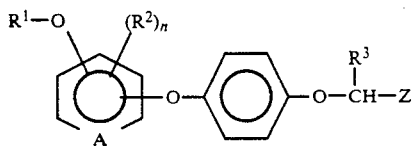

in which
$R^1$ denotes halo($C_1$–$C_8$)alkyl, halo($C_2$–$C_8$)alkenyl or halo($C_2$–$C_6$)alkynyl,
$R^2$ denotes halogen,
n denotes 0 to 3,
A denotes N or N→O,
$R^3$ denotes H or ($C_1$–$C_4$)-alkyl,
Z denotes a group of the formula

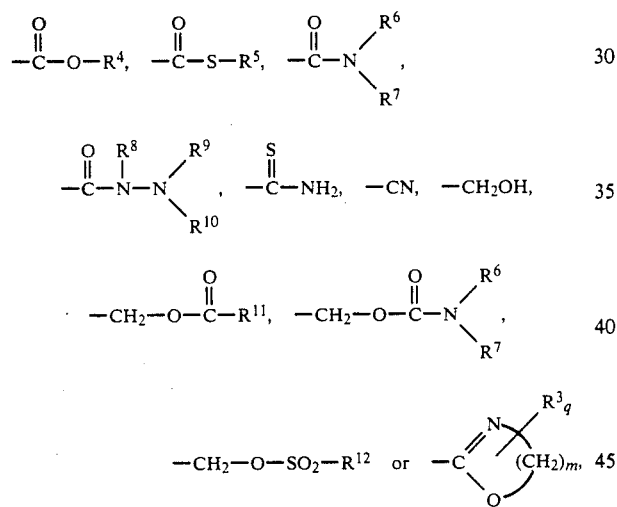

q denotes 0 to 3, m denotes 2 or 3,
$R^4$ denotes H, ($C_1$–$C_{12}$)-alkyl which may optionally be substituted by 1–6 halogen atoms, preferably F, Cl or Br, and/or by OH, CN, SCN, ($C_1$–$C_6$)-alkoxy, ($C_1$–$C_4$)-alkylthio, ($C_1$–$C_4$)-alkylsulfinyl, ($C_1$–$C_4$)-alkylsulfonyl, ($C_1$–$C_6$)-alkoxy-($C_2$–$C_6$)-alkoxy, halo($C_1$–$C_2$)-alkoxy, methoxyethoxyethoxy, ($C_1$–$C_4$)-alkylamino, di-($C_1$–$C_4$)-alkylamino, phenyl, oxiranyl, ($C_1$–$C_4$)-alkoxycarbonyl and/or the

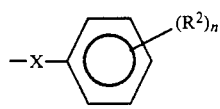

radical;
($C_5$–$C_6$)-cycloalkyl which is optionally substituted by halogen or methyl;
($C_3$–$C_6$)-alkenyl, halo-($C_3$–$C_6$)-alkenyl or ($C_5$–$C_6$)-cycloalkenyl;
($C_3$–$C_4$)-alkynyl which is optionally mono- or disubstituted by ($C_1$–$C_6$)-alkyl, phenyl, halogen or ($C_1$–$C_2$)-alkoxy;
phenyl which is optionally mono- to trisubstituted by ($C_1$–$C_4$)-alkyl, ($C_1$–$C_4$)-alkoxy, halogen, $NO_2$ or $CF_3$; furfuryl, tetrahydrofurfuryl, a cation equivalent of an organic or inorganic base, or one of the groups

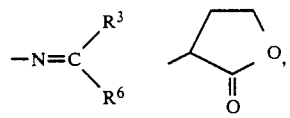

$R^5$ denoted H, ($C_1$–$C_6$)-alkyl, phenyl-($C_1$–$C_2$)-alkyl wherein the phenyl radical may be mono- or disubstituted by ($C_1$–$C_4$)-alkyl and/or halogen; further ($C_3$–$C_6$)-alkenyl, or phenyl which may also be mono- or polysubstituted by ($C_1$–$C_4$)-alkyl and/or halogen,
$R^6$ denotes H, ($C_1$–$C_6$)-alkyl, hydroxy-($C_1$–$C_6$)-alkyl, ($C_5$–$C_6$)-cycloalkyl, or phenyl which is optionally mono- to trisubstituted by ($C_1$–$C_4$)-alkyl, ($C_1$–$C_4$)-alkoxy, halogen or $CF_3$,
$R^7$ has one of the meanings of $R^6$ or may also denote ($C_1$–$C_4$)-alkoxycarbonyl-($C_1$–$C_4$)-alkyl (when $R^6$=H or ($C_1$–$C_6$)-alkyl),
$R^6$ and $R^7$ together denote a methylene chain having 2, 4 or 5 members, in which a $CH_2$ group may be replaced by O, NH or N($CH_3$),
$R^8$ denotes H or $CH_3$,
$R^9$ denotes H, $CH_3$ or $C_2H_5$,
$R^{10}$ denotes H, $CH_3$, $C_2H_5$ or phenyl,
$R^{11}$ denotes ($C_1$–$C_6$)-alkyl which is optionally mono- to trisubstituted by halogen; cyclopropyl, ($C_3$–$C_6$)-alkenyl, phenyl, ($C_1$–$C_4$)-alkylphenyl, ($C_1$–$C_4$)-alkoxyphenyl, halophenyl, trifluoromethylphenyl or nitrophenyl,
$R^{12}$ denotes ($C_1$–$C_4$)-alkyl, or phenyl which may also be mono- or disubstituted by halogen, $CF_3$, $NO_2$ or ($C_1$–$C_4$)-alkyl, and
X denotes O, S, N-($C_1$–$C_4$)-alkyl, NH, —$OCH_2$—, —$NHCH_2$, —N—(($C_1$–$C_4$)-alkyl)-$CH_2$— or —$SCH_2$—.

The haloalkyl, haloalkenyl and haloalkynyl radicals can be either straight-chain or branched. The $R^1$ radical may denote, for example; $CF_2H$, $CF_3$, $CF_2CHF_2$, $CF_2CHFCl$, $CF_2CHFBr$, $CF_2CHFCF_3$, $CH_2CF_3$, $CFCl_2$, $CF_2Cl$, $CH_2Cl$, $CHCl_2$, $CCl_3$, $CHBr_2$, $CH_2CCl$=$CClH$, $CH(CH_3)CH_2Cl$ $CH_2CHClCH_3$, $CH_2CH_2Cl$, $CH_2(CH_2)_2CH_2Cl$. Preferred alkyl radicals are those having 1–2 carbon atoms and, amongst these, fluoroalkyl and/or chlorofluoroalkyl are preferred.

Z is preferably a radical of the formula $COOR^4$, $COSR^5$ or $CONR^6R^7$, where $COOR^4$ is particularly preferred. Above all, H, ($C_1$–$C_6$)-alkyl, particularly methyl or ethyl, alkenyl (allyl), alkynyl (propynyl), haloalkyl or a cation are suitable as the radical $R^4$.

The following may be mentioned as cations: $Na^+$, $K^+$, $Ca^{++}$, $NH_4^+$, $^+NH_3CH_3$, $^+NH_2(CH_3)_2$, $^+NH(CH_3)_3$, $^+N(CH_3)_3$, $^+N(CH_3)_4$, $^+NH(C_2H_5)_3$, $^+NH(C_2H_4OH)_3$, $NH_2(C_6H_5)_2$, $NH_3CH_2C_6H_5$.

The present invention furthermore relates to processes for the preparation of the compounds of the formula I, wherein a) compounds of the formula

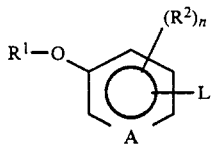

in which L denotes a leaving group such as, for example, halogen, $(C_1-C_4)$-alkylsulfonyl, phenylsulfonyl, $(C_1-C_4)$-alkoxycarbonylmethylsulfonyl, $(C_1-C_4)$-alkylsulfinyl, $(C_1-C_4)$-alkylthio and the mesyl or tosyl radical, are reacted with compounds of the formula

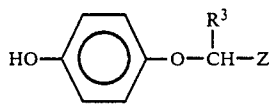

or b) compounds of the formula

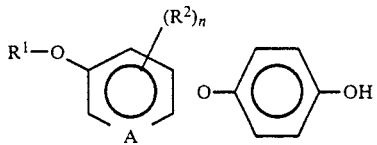

are reacted with compounds of the formula

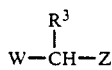

in which W represents halogen (preferably chlorine or bromine) or the mesyl or tosyl radical, or c) compounds of the formula I, in which Z represents the $-COOR^4$ group, are hydrogenated, and the alcohols ($Z=-CH_2OH$) obtained are converted, if desired, into the corresponding carboxylates ($Z=-CH_2-O-C-(O)-R^{11}$) by reaction with carboxylic acids, carboxylic acid halides or anhydrides, into sulfonates ($Z=-CH_2-O-SO_2-R^{12}$) by reaction with sulfonyl halides, or into carbamates

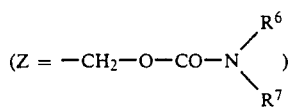

by reaction with carbamoyl halides or isocyanates, or d) the compounds obtained by processes a) and b) are converted into other compounds of the formula I according to the invention by saponification, salt formation, acid chloride preparation and reaction with alcohols, thiols and amines, esterification, transesterification, amidation, elimination of water or hydration, or addition of hydrogen sulfide.

On a) and b)

The reaction of the compounds II and III, and also IV and V, is preferably carried out in inert aprotic solvents, such as aliphatic or aromatic hydrocarbons (such as, for example, benzene, toluene or xylene), acid nitriles such as, for example, acetonitrile or propionitrile, ketones such as, for example, acetone, methyl ethyl ketone or methyl isobutyl ketone, acid amides such as, for example, dimethylformamide, dimethylacetamide, N-methylpyrrolidone or hexamethylphosphoric triamide, or in dimethyl sulfoxide, at temperatures between 30° and 250° C. or the boiling temperature of the solvent, preferably between 60° and 160° C., in the presence of inorganic or organic bases such as, for example, metal alcoholates, tertiary amines, alkali metal or alkaline earth metal carbonates and hydroxides (NaOH or KOH).

On c)

The reduction of acids or esters to alcohols is preferably carried out using complex metal hydrides such as $LiAlH_4$ in ethereal, anhydrous solvents. Since the reaction usually proceeds exothermically, external introduction of heat is generally not necessary. The subsequent esterification using acid anhydrides or acid halides is carried out in inert solvents (such as in the case of a)) at temperatures between 0° C. and the boiling point of the solvents, with addition of an organic or inorganic base, for example $Na_2CO_3$, $K_2CO_3$, pyridine or triethylamine. The esterification using carboxylic acids is carried out either by addition of dehydrating agents such as $P_2O_5$ or by azeotropic extractive distillation of the acidified components. Carbamoyl halides and isocyanates can be reacted with alcohols in the presence of bases under similar conditions as carboxylic acid halides, somewhat higher temperatures generally being used, preferably between 40° C. and the boiling temperature of the solvent.

On d)

One possibility for the amidation of compounds of the formula I is to start from esters and to react these with amines, ammonia or hydrazines. The same solvent as in a) is preferably used in this reaction, which is carried out at temperatures between 40° C. and the reflux temperature. However, another possibility is firstly to convert acids of the formula I into acid halides, in a known manner, and subsequently to react the latter with ammonia, amines or hydrazines. An at least one molar excess of the base employed is necessary to bind the hydrogen halide being liberated. Other esters or thioesters of the formula I can be obtained by reacting the acid chloride with alcohols or mercaptans.

The esterification is carried out by means of acid or basic catalysis. The alcohol which is to be introduced into the ester is expediently added in excess, and the lower-boiling alcohol being liberated is continuously distilled off to the extent in which it is formed during the esterification.

The dehydration of amides to form nitriles is preferably carried out in aromatic hydrocarbons at temperatures from 50° C. to the boiling temperature. The subsequent addition of $H_2S$ is expediently carried out in an autoclave in the presence of catalytic amounts of a base (preferably ethanolamine) at temperatures between 50° and 150° C.

The heterocyclic compounds of the formula II required for the preparation of the compounds of the general formula I according to the invention represent, according to the definition of X, for appropriately substituted 2-halo-, 2-alkylsulfonyl-, 2-phenylsulfonyl-, 2-alkoxycarbonylmethylsulfonyl-, 2-alkylsulfinyl-, 2-alkylthio-, 2-mesyl- or 2-tosylpyridine or pyridine N- oxides, which, for example, can be prepared by addition of haloalkenes or haloalkynes to appropriately substituted halohydroxypyridines.

The corresponding phenols of the formulae III and IV can be prepared, for example, by monoalkylation of hydroquinone (J. Org. Chem. 39, p. 214 (1974) or Soc. 1965, 954–73).

When $R_3$ represents hydrogen, the compounds of the formula I have a center of asymmetry and usually exist in racemic form. The racemates can be separated into enantiomers by conventional methods. However, it is also possible to employ optically active starting materials in the processes mentioned, this being particularly suitable for the reactions according to a) or b), where the compounds III and V are employed in optically active form. The invention relates both to the racemates and to the optical antipodes, particularly the D forms thereof.

The compounds of the general formula I according to the invention are very effective against a wide range of annual and perennial weed grasses when using the pre-emergent and postemergent methods, but they are simultaneously excellently tolerated by dicotyledonous crop plants and by some types of cereal. The compounds are thus suitable, for example, for selective use in crop plants against wild oats (Avena), foxtail (Alopecurus spp.), meadow grass (Poa spp.), rye grass (Lolium spp.), annual and perennial panic grasses (Echinochloa spp., Setaria spp., Digitaria spp., Napicum spp., Sorghum spp.), Bermuda grass (Cynon spp.) and couch grass (Agropyron spp.).

When the compounds according to the invention are used in sub-toxic doses, typical growth-regulating effects can be detected; thus, for example, the growth of the plants, but also the plant contents, can be influenced. The compounds are therefore suitable as growth regulators in crops of useful plants, such as, for example, cereals, maize, sugar beet, tobacco, rice and sorghum. On the other hand, plant covers, such as cultivated lawn or also plant communities at the edges of paths and streets, and also cultivated plants, can also be regulated.

The present invention thus also relates to herbicidal and growth-regulating agents which contain an amount which is effective for herbicidal or growth-regulating purposes of a compound of the general formula I, in addition to conventional additives and formulation auxiliaries.

The agents according to the invention generally contain 2–95% by weight of the active compounds of the formula I. They can be used in the conventional preparations as wettable powders, emulsifiable concentrates, sprayable solutions, dusting agents or granules.

Wettable powders are preparations which can be dispersed uniformly in water and which contain wetting agents, for example polyoxethylated alkylphenols, polyoxyethylated oleylamines and stearylamines, alkyl- or alkylphenylsulfonates and dispersing agents, for example sodium ligninsulfonate, sodium 2,2'-dinaphthylmethane-6,6'-disulfonate, or also sodium oleylmethyltaurinate, besides the active compound and in addition to a diluent or inert material.

Emulsifiable concentrates are obtained by dissolving the active compound in an organic solvent, for example butanol, cyclohexanone, dimethylformamide, xylene or higher-boiling aromatics, and adding a non-ionic wetting agent, for example a polyoxethylated alkylphenol or a polyoxethylated oleylamine or stearylamine.

Dusting agents are obtained by grinding the active compound with finely divided, solid substances, for example talcum, natural clays, such as kaolin, bentonite, pyrophillite or diatomaceous earths.

Sprayable solutions, as are frequently sold in spray cans, contain the active compound dissolved in an organic solvent, and, for example, a mixture of fluorochlorohydrocarbons is also present as propellant.

Granules can either be prepared by atomizing the active compound onto adsorptive, granulated inert material or by applying active compound concentrates onto the surface of carrier materials, such as sand, kaolinite, or of granulated inert material, by means of adhesives, for example polyvinyl alcohol or sodium polyacrylate, or alternatively mineral oils. Suitable active compounds may also be prepared—if desired as a mixture with fertilizers—in the fashion which is conventional for the preparation of fertilizer granules.

In the case of the herbicidal agents, the concentrations of the active compounds can vary in the commercially available formulations. In wettable powders, the active compound concentrations vary, for example, between 10% and 95%, the remainder comprising the abovementioned formulation additives. In the case of emulsifiable concentrates, the active compound concentration is about 10% to 80%. Dusty . . . (sic) sprayable solutions about 2 to 20%. In the case of granules, the active compound content depends partly on whether the active compound is liquid or solid and on which granulation auxiliaries, fillers etc. are used.

For use, the commercially available concentrates are diluted, if appropriate, in a conventional fashion, in the case of wettable powders and emulsificable concentrates, for example, using water. Dusty and granulated preparations, and also sprayable solutions, are not diluted further with further inert materials before use. The applicational amount necessary varies with the external conditions, such as temperatures and humidity, inter alia. It can vary within wide limits and is 0.01 to 10 kg/ha for herbicidal agents and 0.001 to 1 kg/ha for growth-regulating agents.

The active compounds according to the invention can be combined with other herbicides, insecticides and fungicides.

A. Formulation Examples

EXAMPLE A

An emulsifiable concentrate is obtained from
15 parts by weight of active compound
75 parts by weight of cyclohexanone as solvent and
10 parts by weight of oxethylated nonylphenol (10 EO) as emulsifier.

EXAMPLE B

A wettable powder which is easily dispersible in water is obtained by mixing
25 parts by weight of active compound
64 parts by weight of kaolin-containing quartz as inert material
10 parts by weight of calcium ligninsulfonate and
1 part by weight of sodium oleylmethyltaurinate as wetting and dispersing agent,
and grinding in a disk attrition mill.

EXAMPLE C

A dusting agent is obtained by mixing
10 parts by weight of active compound and 90 parts by weight of talc as inert material, and comminuting in a hammer mill.

EXAMPLE D

A granulate comprises, for example, about
2-15 parts by weight of active compound and
98-85 parts by weight of inert granulated materials, such as, for example, attapulgite, pumice stone and quartz sand.

B. Chemical Examples
EXAMPLE 1

Ethyl 2-(4-(5-chloro-3-(2-chloro-1,1,2-trifluoroethoxy)-2-pyridyloxy)-phenoxy)propionate 9.75 g (30 mmol) of 2-bromo-5-chloro-3-(2-chloro-1,1,2-trifluoroethoxy)pyridine, 6.94 g (33 mmol) of ethyl 4-hydroxyphenoxypropionate and 6.6 g of anhydrous potassium carbonate in 40 ml of absolute dimethyl sulfoxide were stirred for 9 hours at 80° C. under argon. After cooling, the mixture was diluted with 300 ml of diethyl ether, the potassium carbonate was filtered off, and the organic phase was washed with 5% strength KOH and subsequently with water until neutral. After drying, the compound of Example 1 was obtained in a crude yield of 13.4 g (98% of theory).

The crude product was chromatographed over silica gel (eluent methylene chloride). The purified product had an $n_D^{20}$ of 1.5227. The purity and structure were confirmed—as also in the case of the following compounds—by thin layer chromatography and NMR spectroscopy respectively.

The following compounds are obtained in an analogous fashion:

TABLE 1

| Ex. No. | $R^1$ | A | $R^2$ | Z | b.p.: [°C.] m.p.; $n_D$ |
|---|---|---|---|---|---|
| 2 | $CF_2H$ | N | Cl | $COOC_2H_5$ | $n_D^{20}$: 1.4898 |
| 3 | $CF_2CHClF$ | N | Cl | $COOC_2H_5$ | $n_D^{20}$: 1.5000 |
| 4 | $CF_2CHF_2$ | N | Cl | $COOC_2H_5$ | $n_D^{20}$: 1.5030 |
| 5 | $CF_2H$ | N | Cl | COOH | |
| 6 | $CF_2H$ | N | Cl | $COOCH_3$ | |
| 7 | $CF_2H$ | N | Cl | $COOC_3H_7$ | |
| 8 | $CF_2H$ | N | Cl | $COOC_4H_9$ | |
| 9 | $CF_2H$ | N | Cl | $COOCH_2CH_2OCH_3$ | |
| 10 | $CF_3$ (D isomer) | N | Cl | $COOC_2H_5$ | $[\alpha]_D^{20}$: 21.6° (C = 20; $CH_2Cl_2$) |
| 11 | $CF_3$ | N | H | $COOC_2H_5$ | $n_D^{20}$: 1.5280 |
| 12 | $CF_2H$ | N | Cl | $COOCH(CH_3)C_2H_5$ | |
| 13 | $CF_2H$ | N | Cl | COO—⟨C6H11⟩ | |
| 14 | $CF_2H$ | N | Cl | $COOCH_2CH=CH_2$ | |
| 15 | $CF_2H$ | N | Cl | $COOCH_2-C\equiv CH$ | |
| 16 | $CF_2H$ | N | Cl | $COON=C(CH_3)_2$ | |
| 17 | $CF_2H$ | N | Cl | $COSC_2H_5$ | |
| 18 | $CF_2H$ | N | Cl | $COOCH_2CH_2Cl$ | |
| 19 | $CF_2H$ | N | Cl | $COOCH_2-C_6H_5$ | |
| 20 | $CF_2H$ | N | Cl | $COOCH_2COOH_3$ | |
| 21 | $CF_2H$ | N | Cl | $COOCH(CH_3)COOC_2H_5$ | |
| 22 | $CF_2H$ | N | Cl | $CONH_2$ | |
| 23 | $CF_2H$ | N | Cl | $CONHCH_3$ | |
| 24 | $CF_2H$ | N | Cl | $CON(CH_3)_2$ | |
| 25 | $CF_2H$ | N | Cl | $CONHCH_2CH=CH_2$ | |
| 26 | $CF_2H$ | N | Cl | $CONHC_6H_5$ | |
| 27 | $CF_2H$ | N | Cl | CON—⟨C6H11⟩ | |
| 28 | $CF_2H$ | N | H | $COOC_2H_5$ | |
| 29 | $CF_2H$ | N | H | $COOCH_3$ | |
| 30 | $CF_2H$ | N | H | COOH | |
| 31 | $CF_2H$ | N | Cl | COOK | |
| 32 | $CCl_3$ | N | Cl | $COOC_2H_5$ | |
| 33 | $CF_3$ | N | Cl | $COOC_3H_7$ (n) | |
| 34 | $CF_3$ | N | Cl | $COOC_2H_5$ | |
| 35 | $CF_2Cl$ | N | Cl | $COOCH_2CH=CH_2$ | |
| 36 | $CF_2H$ | N | Cl | $COOCH_2CH_2OCH_2C_6H_5$ | |
| 37 | $CF_2H$ | N | Cl | $COOCH_2CH_2N(CH_3)CH_2C_6H_5$ | |
| 38 | $CF_3$ | N | Cl | $COOCH_2SCH_3$ | |

TABLE 1-continued

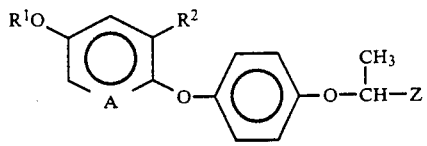

| Ex. No. | R¹ | A | R² | Z | b.p.; [°C.] m.p.; $n_D$ |
|---|---|---|---|---|---|
| 39 | $CF_2CF_2H$ | N | Cl | COOH | |
| 40 | $CF_2Cl$ | N | Cl | $COOC_2H_5$ | $n_D^{20}$: 1.5970 |
| 41 | $CF_2CHClF$ | N | Cl | $COOC_2H_5$ | |
| 42 | $CH_2CF_3$ | N | Cl | COONa | |
| 43 | $CH_2CH_2Cl$ | N | Cl | $COOC_2H_5$ | |
| 44 | $CH_2CH_2F$ | N | Cl | $COOH_3$ | |
| 45 | $CF_2H$ | N | Cl | $COOC_2H_5$ (D isomer) | |

C. Biological Examples

EXAMPLE I pre-emergent treatment

Grass seeds were sown in pots and the preparations according to the invention, formulated as wettable powders or as emulsion concentrates, were sprayed onto the surface of the crop soil in various dosages. The pots were subsequently placed in a greenhouse for 4 weeks and the result of the treatment (as in the following examples) determined by classification according to the scale below:

| 0 | 0% damage |
|---|---|
| 1 > 0 | 20% damage |
| 2 > 20 | 40% damage |
| 3 > 40 | 60% damage |
| 4 > 60 | 80% damage |
| 5 > 80 | 100% damage |

The preparations according to the invention exhibit a good action against annual weed grasses, and also against some perennial weed grasses; Avena, Alopecurus, Lolium, Echinochloa, Setaria, Agropyron and Cynodon were used as test plants.

The active compounds according to the invention exhibited good action in this test model (see Table 2).

EXAMPLE II post-emergent treatment

Grass seeds were sown in pots and germinated in a greenhouse. 3 weeks after sowing, the preparations according to the invention, formulated as wettable powders or as emulsion concentrates, were sprayed onto the plants in various dosages, and the action of the preparations was classified after 4 weeks standing in the greenhouse.

The active compounds according to the invention had a good herbicidal action against a broad spectrum of annual weed grasses (see Table 3). Furthermore, some compounds also combated the perennial weed grasses Cynodon dactylon, Sorghum halepense and Agropyron repens.

TABLE 2

| | | Pre-emergent action | | | | | |
|---|---|---|---|---|---|---|---|
| Example | Dose kg of a.i./ha | Herbicidal action | | | | | |
| | | POA | AVF | ALM | SAL | LOM | ECG |
| 2 | 2.4 | 5 | 5 | 5 | 5 | 5 | 5 |
| | 0.6 | 5 | 5 | 5 | 5 | 5 | 5 |
| 4 | 2.4 | 5 | 5 | 5 | 5 | 5 | 5 |
| 10 | 2.4 | 5 | 5 | 5 | 5 | 5 | 5 |
| | 0.6 | 5 | 5 | 5 | 5 | 5 | 5 |
| 40 | 2.4 | 5 | 5 | 5 | 5 | 5 | 5 |
| | 0.6 | 5 | 3 | 5 | 5 | 3 | 4 |

TABLE 3

| | | Post-emergent action | | | | | |
|---|---|---|---|---|---|---|---|
| Example | Dose kg of a.i./ha | Herbicidal action | | | | | |
| | | POA | AVE | ALM | SAL | LOM | ECG |
| 2 | 2.4 | 5 | 5 | 5 | 5 | 5 | 5 |
| | 0.6 | 5 | 5 | 5 | 5 | 5 | 5 |
| 4 | 2.4 | — | 5 | 5 | 5 | 5 | 5 |
| | 0.6 | — | 5 | 5 | 3 | 4 | 5 |
| 10 | 2.4 | 5 | 5 | 5 | 5 | 5 | 5 |
| | 0.6 | 5 | 5 | 5 | 5 | 5 | 5 |
| 40 | 2.4 | 5 | 5 | 5 | 5 | 5 | 5 |
| | 0.6 | 5 | 5 | 5 | 5 | 5 | 5 |

Abbreviations:
POA = Poa annua (meadow grass)
AVF = Avena fatua (wild oat)
ALM = Alopecurus myosuroides blackgrass
SAL = Setaria lutescens (yellow foxtail)
LOM = Lolium multiflorum (rye grass)
ECG = Echinochloa crus-galli (barnyard grass)
a.i. = active ingredient

EXAMPLE III crop plant compatibility

In further experiments in the greenhouse, seeds of a relatively large number of crop plants were placed in pots. Some of the pots were treated immediately, and the rest were placed in a greenhouse and sprayed with substances according to the invention when the plants had developed 2 or 3 true leaves.

The results which were determined 4 to 5 weeks after application show that the substances according to the invention do not damage dicotyledonous crops when the pre- and post-emergent methods are used. In addition, some substances also protect gramineous crops such as barley, sorghum, maize, wheat or rice.

TABLE 4

| Example | Dose kg/ha | Action against BV | GS | BN |
| --- | --- | --- | --- | --- |
| 2 | 2.4 | 0 | 0 | 0 |
| 4 | 2.4 | 0 | 0 | 0 |
| 10 | 2.4 | 0 | 0 | 0 |
| 40 | 2.4 | 0 | 0 | 0 |

Abbreviations:
BV = *Beta vulgaris* (sugar beet)
GS = *Glycine soya* (soya bean)
BN = *Brassica napa* (rape seed)

We claim:
1. A compound of the formula

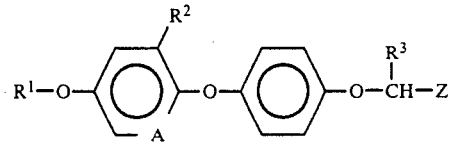

in which
$R^1$ is $CF_2H$,
$R^2$ is Cl,
A is N,
$R^3$ is methyl,
Z is a group of the formula

and
$R^4$ is $CH_2-C\equiv CH$.

2. A compound of the formula

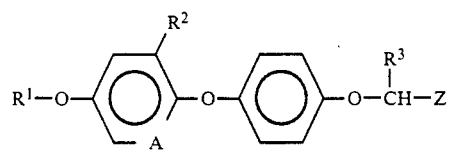

in which
$R^1$ is $CF_3$,
$R^2$ is Cl,
A is N,
$R^3$ is methyl,
Z is a group of the formula

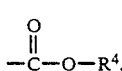

and
$R^4$ is $CH_2-C\equiv CH$.

3. A compound of the formula

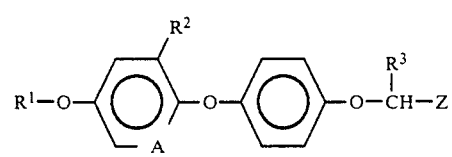

in which
$R^1$ is $CF_2H$,
$R^2$ is Cl,
A is N,
$R^3$ is methyl,
Z is a group of the formula

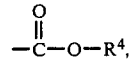

and
$R^4$ is $C_2H_5$.

4. A compound of the formula I

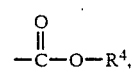

which is the D-isomer in which
$R^1$ is $CF_2H$,
$R^2$ is Cl,
A is N,
$R^3$ is methyl,
Z is a group of the formula

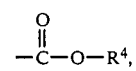

and
$R^4$ is $C_2H_5$.

5. A compound of the formula I

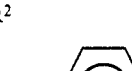

in which
$R^1$ is $CF_3$,
$R^2$ is Cl,
A is N,
$R^3$ is methyl,
Z is a group of the formula

—C(=O)—O—$R^4$, and
$R^4$ is $C_2H_5$.

6. A compound of the formula I in which
$R^1$ is $CF_2Cl$,
$R^2$ is Cl,
A is N,
$R^3$ is methyl,
Z is a group of the formula

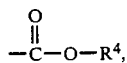

and

R⁴ is C₂H₅.

7. A compound of the formula

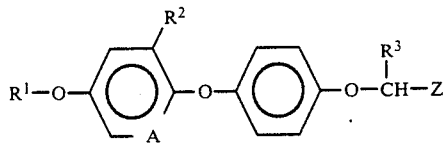

in which

R¹ is (C₁–C₈)-haloalkyl,

R² is halogen,

A is N,

R³ is methyl,

Z is a group of the formula

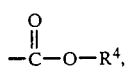

and

R⁴ is (C₁–C₆)-alkyl.

8. A compound of the formula

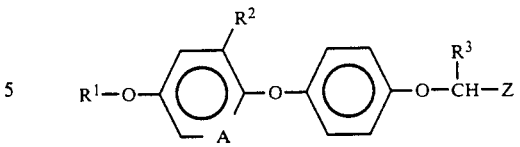

in which

R¹ is (C₁–C₈)-haloalkyl,

R² is halogen,

A is N,

R³ is methyl,

Z is a group of the formula

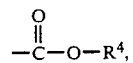

and

R⁴ is ethyl.

9. A compound of the formula

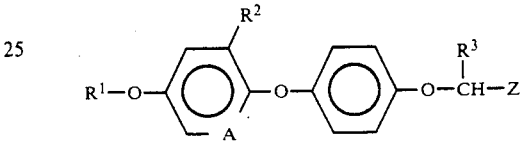

in which

R¹ is (C₁–C₈)-haloalkyl,

R² is halogen,

A is N,

R³ is methyl,

Z is a group of the formula

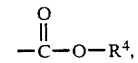

and

R⁴ is CH₂—C≡CH.

* * * * *